Figure 1:
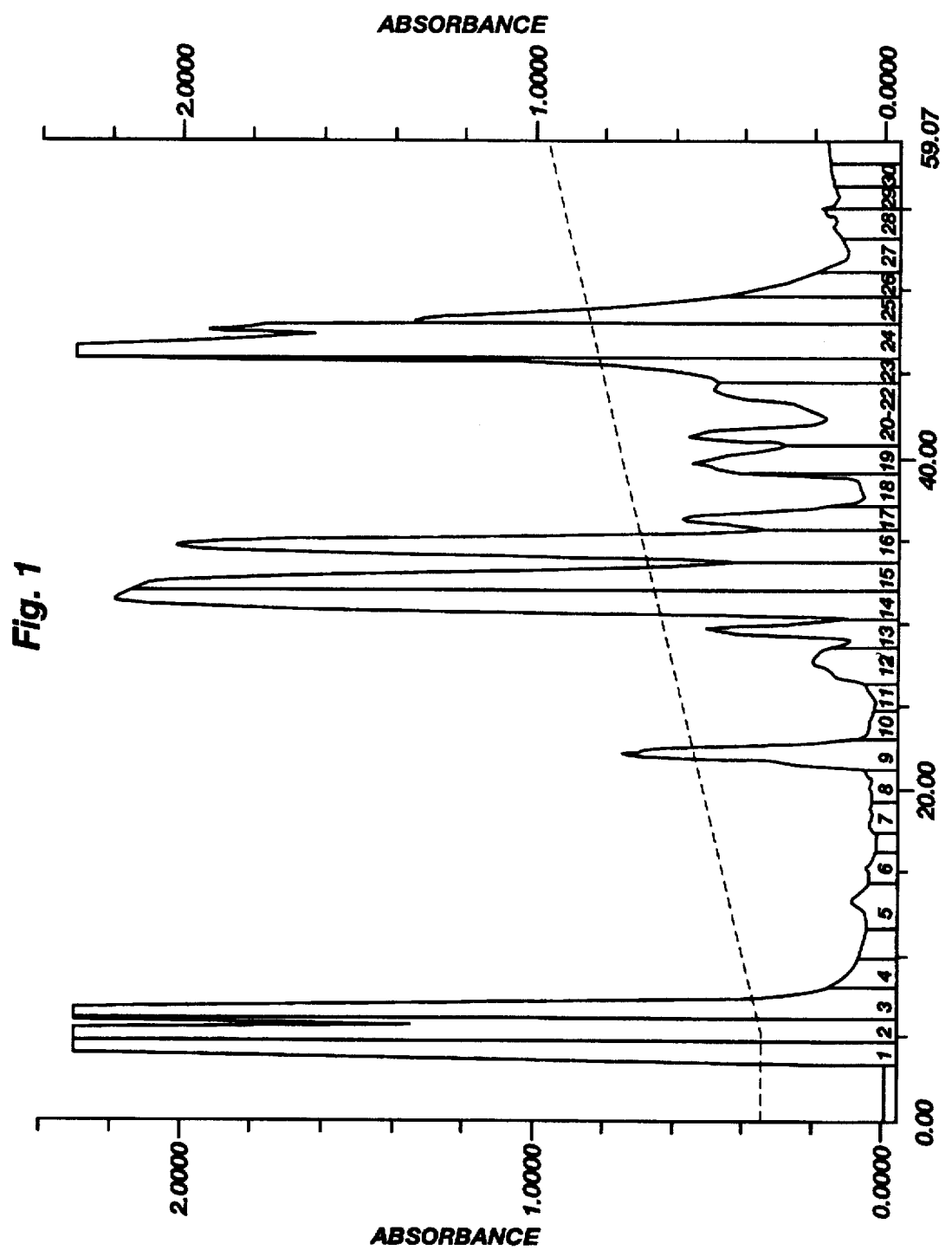
Figure 2:
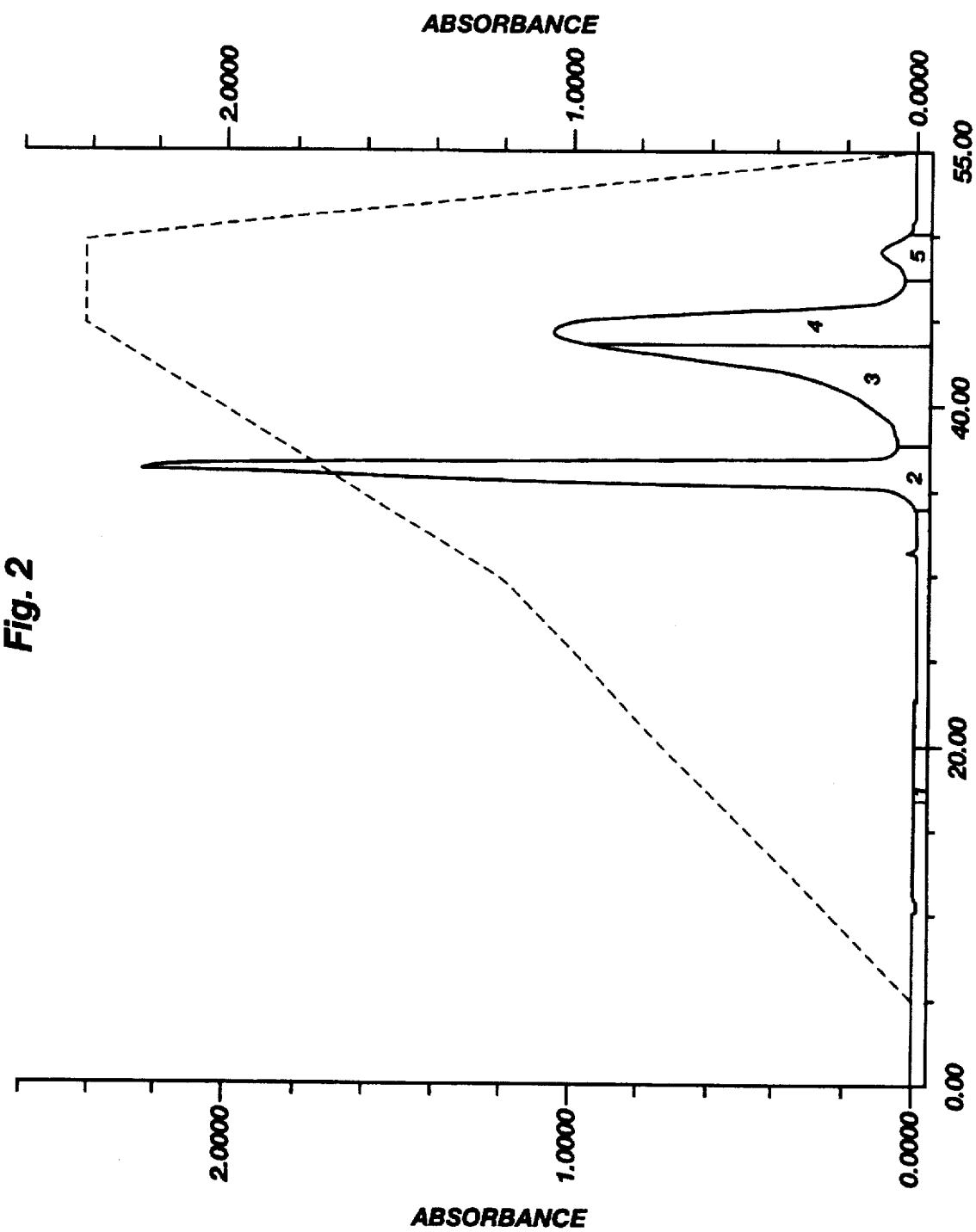
Figure 3:
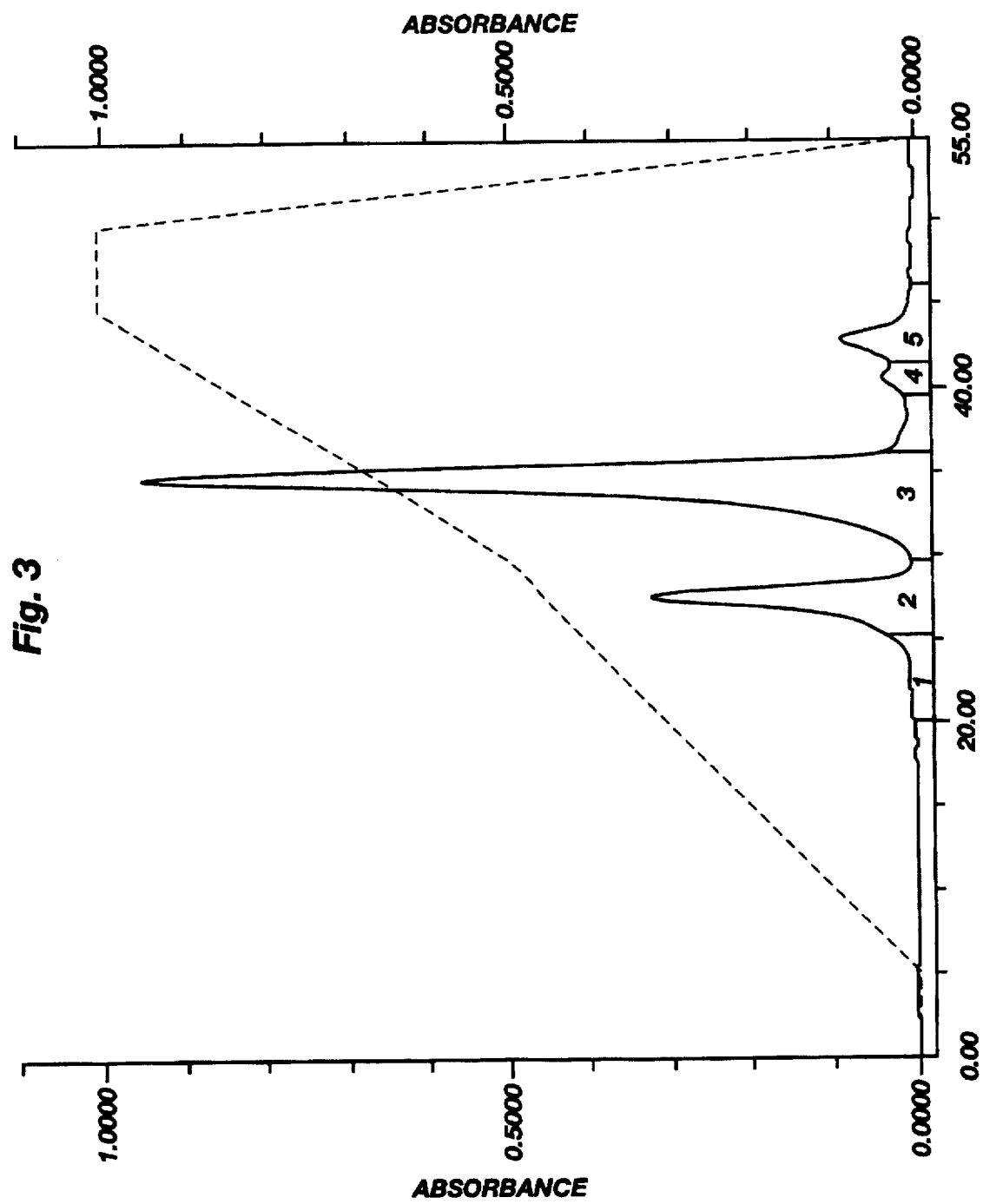

United States Patent [19]
Johnson et al.

[11] Patent Number: 5,688,764
[45] Date of Patent: Nov. 18, 1997

[54] INSECTICIDAL PEPTIDES FROM SPIDER VENOM

[75] Inventors: Janice H. Johnson; Robert M. Kral, Jr.; Karen Krapcho, all of Salt Lake City, Utah

[73] Assignee: NPS Pharmaceuticals, Inc., Salt Lake City, Utah

[21] Appl. No.: 390,882

[22] Filed: Feb. 17, 1995

[51] Int. Cl.$^6$ .................... A01N 37/18; C07K 14/435; C12N 1/00; C12N 5/10; C12N 15/12; C12N 15/63
[52] U.S. Cl. ................... 514/12; 514/2; 530/300; 530/858; 536/23.5; 435/172.3; 435/69.1; 435/320.1; 435/240.1; 435/252.3; 435/254.11
[58] Field of Search .................... 536/23.5; 435/172.3, 435/69.1, 320.1, 252.3, 254.11, 240.1; 530/300, 858; 514/12, 2

[56] References Cited

U.S. PATENT DOCUMENTS

| | | | |
|---|---|---|---|
| 4,925,664 | 5/1990 | Jackson et al. | 424/537 |
| 5,037,846 | 8/1991 | Sacomano et al. | 514/419 |
| 5,185,369 | 2/1993 | Saccomano et al. | 514/502 |
| 5,227,397 | 7/1993 | Saccomano et al. | 514/419 |

FOREIGN PATENT DOCUMENTS

| | | |
|---|---|---|
| 2005658 | 6/1990 | Canada. |
| WO93/18145 | 9/1993 | WIPO. |

OTHER PUBLICATIONS

"Overproduction of Encapsulated Insecticidal Crystal Proteins in a *Bacillus thuringiensis spoOA* Mutant", Lereclus et al., *Bio/Technology*, vol. 13, Jan. 13, 1995, p. 67.

"Insecticidal Activity of Spider (Araneae), Centipede (Chilopoda), Scorpion (Scorpionida), and Snake (Serpentes) Venoms", Quistad et al., *Journal of Economic Entomology*, vol. 85, No. 1, Feb. 1992, pp. 33–39.

"Development of a Recombinant Baculovirus Expressing an Insect–Selective Neurotoxin: Potential for Pest Control", McCutchen et al., *Bio/Technology*, vol. 9, Sep. 1991, pp. 848–852.

"Identification of Insecticidal Peptides from Venom of the Trap–Door Spider, *Aptostichus schlingeri* (Ctenizidae)", Skinner et al., *Toxicon*, vol. 30, No. 9, 1992, pp. 1043–1050.

"Neurotoxins from Venoms of the Hymenoptera–Twenty-–Five Years of Research in Amsterdam", Tom Piek, *Comp. Biochem. Physiol.*, vol. 96C, No. 2, 1990, pp. 223–233.

"Curatoxins, Neurotoxic Insecticidal Polypeptides Isolated From the Funnel–Web Spider *Holonea curta*", Stapleton et al., *The Journal of Biological Chemistry*, vol. 265, No. 4, Feb. 5, 1990, pp. 2054–2059.

"Signal Sequences", Lila M. Gierasch, *Biochemistry*, vol. 28, No. 3, Feb. 7, 1989, pp. 923–030.

"Purification and Characterization of Two Classes of Neurotoxins from the Funnel Web Spider, *Agelenopsis aperta*", Skinner et al., *The Journal of Biological Chemistry*, vol. 264, No. 4, Feb. 5, 1989, pp. 2150–2155.

"Trends in the Development of Baculovirus Expression Vectors", Luckow et al., *Bio/Technology*, vol. 6, Jan. 1988, pp. 47–55.

"The Action of a Toxin From the Venom of the Wasp *Habrobracon hebetor* (SAY) on the Neuromuscular Transmission of Insects", Slavnova et al., Apr. 16, 1987, Doklady Biological Sciences (English translation vo. 297 No. 1–6 pp. 684–686.

"Characterization of Two Paralysing Proteins Toxins (A–MTX and B–MTX), Isolated from a Homogenate of the Wasp *Microbracon hebetor* (SAY)", Visser et al., *Comp. Biochem. Physiol.*, vol. 75B, No. 3, 1983, pp. 523–530.

"Two Different Paralysing Preparations Obtained from a Homogenate of the Wasp *Microbracon hebetor* (SAY)", Spanjer et al., *Toxicon*, vol. 15, (1977) pp. 413–421.

"Isolation and Some Biochemical Properties of a Paralysing Toxin from the Venom of the Wasp *Microbracon hebetor* (SAY)", Visser et al., *Toxicon*, vol. 14, 1976, pp. 357–370.

"Short Communication Stability of *Microbracon hebetor* (SAY) Venom Preparations", D. Drenth, *Toxicon*, vol. 12, pp. 541–542 (1974).

*Primary Examiner*—Robert A. Wax
*Assistant Examiner*—G. E. Bugaisky
*Attorney, Agent, or Firm*—Madson & Metcalf

[57] ABSTRACT

This invention relates to the purification of a family of insecticidally effective peptides isolated from the spider, Calisoga sp., characterized by their neurotoxic effect on insect pest and low mammalian toxicity. The cDNA sequences for three of these peptides have been isolated, and the complete coding sequence is provided. This invention also discloses methods for producing recombinant peptides, as well as methods of utilizing these peptides as insecticidal agents.

38 Claims, 4 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
  ( A ) LENGTH: 39 amino acids
  ( B ) TYPE: amino acids
  ( C ) STRANDEDNESS: single
  ( D ) TOPOLOGY: unknown ( i i ) MOLECULE TYPE: peptide ( i i i ) HYPOTHETICAL:

( i v ) ANTI-SENSE: no ( v ) FRAGMENT TYPE:

( v i ) ORIGINAL SOURCE:
  ( A ) ORGANISM: Calisoga sp.
  ( C ) INDIVIDUAL ISOLATE: peptide A
  ( I ) ORGANELLE: Venom glands ( x i ) SEQUENCE DESCRIPTION: SEQ ID NO:1:

```
Cys Ile Ser Ala Arg Tyr Pro Cys Ser Asn Ser Lys Asp Cys Cys
 1               5                  10                  15

Ser Gly Asn Cys Gly Thr Phe Trp Thr Cys Tyr Ile Arg Lys Asp
                 20                  25                  30

Pro Cys Ser Lys Glu Cys Leu Ala Pro
                 35
```

( 2 ) INFORMATION FOR SEQ ID NO:2:

( i ) SEQUENCE CHARACTERISTICS:
    ( A ) LENGTH: 39 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL:

( i v ) ANTI-SENSE: no ( v ) FRAGMENT TYPE:

( v i ) ORIGINAL SOURCE:
    ( A ) ORGANISM: Calisoga sp.
    ( C ) INDIVIDUAL ISOLATE: peptide B
    ( I ) ORGANELLE: Venom glands ( x i ) SEQUENCE DESCRIPTION: SEQ ID NO:2:

```
Cys Ile Ser Ala Arg Tyr Pro Cys Ser Asn Ser Lys Asp Cys Cys
 1               5                  10                  15

Ser Gly Asn Cys Gly Thr Phe Trp Thr Cys Phe Ile Arg Lys Asp
                 20                  25                  30

Pro Cys Ser Lys Glu Cys Leu Ala Pro
                 35
```

( 2 ) INFORMATION FOR SEQ ID NO:3:

( i ) SEQUENCE CHARACTERISTICS:
    ( A ) LENGTH: 39 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL:

( i v ) ANTI-SENSE: no ( v ) FRAGMENT TYPE:

(vi) ORIGINAL SOURCE:
  (A) ORGANISM: Calisoga sp.
  (C) INDIVIDUAL ISOLATE: peptide C
  (I) ORGANELLE: Venom glands (xi) SEQUENCE DESCRIPTION: SEQ ID NO:3:

```
Cys Ile Ser Ala Arg Tyr Pro Cys Ser Asn Ser Lys Asp Cys Cys
1               5                   10                  15

Ser Gly Ser Cys Gly Ile Phe Trp Thr Cys Tyr Leu Arg Lys Asp
                20                  25                  30

Pro Cys Ser Lys Glu Cys Leu Ala Pro
                35
```

(2) INFORMATION FOR SEQ ID NO:4:

(i) SEQUENCE CHARACTERISTICS:
    (A) LENGTH: 23 base pairs
    (B) TYPE: Nucleic acid
    (C) STRANDEDNESS: single
    (D) TOPOLOGY: unknown (ii) MOLECULE TYPE: synthetic oligonucleotide (iii) HYPOTHETICAL:

(iv) ANTI-SENSE: no (v) FRAGMENT TYPE:

(ix) FEATURE:
    (D) OTHER INFORMATION: According to abbreviations set forth
        in Sec. 1.822 (p)(1) base number 9 represented by the
        letter N corresponds to the modified base inosine(i).

(xi) SEQUENCE DESCRIPTION: SEQ ID NO:4:

ATGATWWSNG C YMGNTA Y CC MTG    23

(2) INFORMATION FOR SEQ ID NO:5:

(i) SEQUENCE CHARACTERISTICS:
    (A) LENGTH: 397 base pairs
    (B) TYPE: Nucleic acid
    (C) STRANDEDNESS: Double
    (D) TOPOLOGY: unknown (ii) MOLECULE TYPE: cDNA (iii) HYPOTHETICAL:

(iv) ANTI-SENSE: yes (v) FRAGMENT TYPE:

(vi) ORIGINAL SOURCE:
    (A) ORGANISM: Calisoga sp.
    (C) INDIVIDUAL ISOLATE: peptide A cDNA
    (I) ORGANELLE: Venom glands (xi) SEQUENCE DESCRIPTION: SEQ ID NO:5:

```
AAAATTTTCT TCACGTTCAT CATAGTTGCA GTAAGTTGGA TTACAGTGTC                50

TTACATG ATG AAG TAC TTC GTT GTC TTC TGT GTG CTG ATC ATC          93
              Met Lys Tyr Phe Val Val Phe Cys Val Leu Ile Ile
              -40              -35                      -30

GCA GTT GCT GCA TTT ACA TCT GCT GCT GAA GAC GGA GAA GTC         135
      Ala Val Ala Ala Phe Thr Ser Ala Ala Glu Asp Gly Glu Val
                      -25                  -20

TTT GAG GAA AAT CCG TTG GAA TTC CCA AAG ACC ATA CAA AAA         177
      Phe Glu Glu Asn Pro Leu Glu Phe Pro Lys Thr Ile Gln Lys
      -15                  -10                  -5
```

```
AGA TGC ATA TCG GCT CGT TAT CCA TGT TCA AAT TCC AAA GAC          219
Arg Cys Ile Ser Ala Arg Tyr Pro Cys Ser Asn Ser Lys Asp
  1           5                    10

TGC TGT AGC GGA AAC TGT GGT ACC TTT TGG ACT TGT TAC ATC          261
Cys Cys Ser Gly Asn Cys Gly Thr Phe Trp Thr Cys Tyr Ile
     15              20                   25

AGA AAA GAT CCG TGC TCT AAA GAA TGT CTT GCG CCT                  297
Arg Lys Asp Pro Cys Ser Lys Glu Cys Leu Ala Pro
         30                 35

TAGAAGCAAA GTTCGTCGC TAAACTGAAA AGTTATTTTG TTACGGCACA            347

AAATCAACAG ATATGTCAGT GCACGTAAAA TAAATGAATT CCATTCTCCG            397
```

( 2 ) INFORMATION FOR SEQ ID NO:6:

( i ) SEQUENCE CHARACTERISTICS:
        ( A ) LENGTH: 217 base pairs
        ( B ) TYPE: Nucleic acid
        ( C ) STRANDEDNESS: Double
        ( D ) TOPOLOGY: unknown ( i i ) MOLECULE TYPE: cDNA ( i i i ) HYPOTHETICAL:

( i v ) ANTI-SENSE: yes ( v ) FRAGMENT TYPE:

( v i ) ORIGINAL SOURCE:
        ( A ) ORGANISM: Calisoga sp.
        ( C ) INDIVIDUAL ISOLATE: peptide B cDNA
        ( I ) ORGANELLE: Venom glands ( x i ) SEQUENCE DESCRIPTION: SEQ ID NO:6:

```
TGC ATA TCG GCT CGT TAT CCA TGT TCA AAT TCC AAA GAC TGC TGT       45
Cys Ile Ser Ala Arg Tyr Pro Cys Ser Asn Ser Lys Asp Cys Cys
  1           5                    10                  15

AGC GGA AAC TGT GGT ACC TTT TGG ACT TGT TTC ATC AGA AAA GAT       90
Ser Gly Asn Cys Gly Thr Phe Trp Thr Cys Phe Ile Arg Lys Asp
              20                   25                  30

CCG TGC TCT AAA GAA TGT CTT GCG CCT                              117
Pro Cys Ser Lys Glu Cys Leu Ala Pro
             35

TAGAAGCAAA GTTCGTCGC TAAACTGAAA AGTTATTTTG TTACGGCACA            167

AAATCAACAG ATATGTCAGT GCACGTAAAA TAAATGAATT CCATTCTCCG            217
```

( 2 ) INFORMATION FOR SEQ ID NO:7:

( i ) SEQUENCE CHARACTERISTICS:
        ( A ) LENGTH: 217 base pairs
        ( B ) TYPE: Nucleic acid
        ( C ) STRANDEDNESS: Double
        ( D ) TOPOLOGY: unknown ( i i ) MOLECULE TYPE: cDNA ( i i i ) HYPOTHETICAL:

( i v ) ANTI-SENSE: yes ( v ) FRAGMENT TYPE:

( v i ) ORIGINAL SOURCE:
        ( A ) ORGANISM: Calisoga sp.
        ( C ) INDIVIDUAL ISOLATE: peptide C cDNA
        ( I ) ORGANELLE: Venom glands ( x i ) SEQUENCE DESCRIPTION: SEQ ID NO:7:

-continued

| | | | | | | | | | | | | | | |
|---|---|---|---|---|---|---|---|---|---|---|---|---|---|---|
| TGC | ATA | TCG | GCT | CGT | TAT | CCA | TGT | TCA | AAT | TCC | AAA | GAC | TGC | TGT | 45
| Cys | Ile | Ser | Ala | Arg | Tyr | Pro | Cys | Ser | Asn | Ser | Lys | Asp | Cys | Cys |
| 1 | | | | 5 | | | | | 10 | | | | | 15 |
| AGC | GGA | AGC | TGT | GGT | ATC | TTT | TGG | ACT | TGT | TAC | CTC | AGA | AAA | GAT | 90
| Ser | Gly | Ser | Cys | Gly | Ile | Phe | Trp | Thr | Cys | Tyr | Leu | Arg | Lys | Asp |
| | | | | 20 | | | | | 25 | | | | | 30 |
| CCG | TGC | TCT | AAA | GAA | TGT | CTT | GCG | CCT | | | | | | | 117
| Pro | Cys | Ser | Lys | Glu | Cys | Leu | Ala | Pro |
| | | | | 35 |

| | | | | |
|---|---|---|---|---|
| TAGAAGCAAA | GTTTCGTCGC | TAAACTGAAA | AGTTATTTTG | TTACGGCACA | 167
| AAATCAACAG | ATATGTCAGT | GCACGTAAAA | TAAATGAATT | CCATTCTCCG | 217

INSECTICIDAL PEPTIDES FROM SPIDER VENOM

FIELD OF THE INVENTION

The present invention is related to peptides isolated from spider venom which display insecticidal characteristics. More particularly, the present invention relates to a family of insecticidally effective peptides isolated from the spider Calisoga sp., characterized by their neurotoxic effect on specific insect pests.

BACKGROUND OF THE INVENTION

Insects destroy about one third of global agricultural production each year. The impact on the lives of millions of people around the world could not be more significant. Insects are also well known as carriers of serious human and animal diseases. Thus, two of the most significant human problems, disease and hunger, are directly and seriously impacted by the activity of insects.

As a result of these activities of insects, insecticides play a crucial role in preserving the world's food supply and in minimizing the spread of serious human diseases. In the past, chemical insecticides such as DDT, chlordane and cyclodienes were widely used to control insects. The toxicity of these insecticides is not specific to insects, however, but may also harm wildlife and threaten human health. Many of these insecticides have been classified as carcinogens. Other chemical insecticides have been implicated in respiratory, immune, nervous, blood, liver, and heart disorders. Thus, traditional chemical insecticides have some serious inherent limitations. Importantly, some of these limitations only manifest themselves years after the chemical has been used in the context of insect control.

Newer types of chemical insecticides, such as the synthetic pyrethroids, are highly effective against insect pests and are relatively harmless to mammals. Insects, however, have shown the capacity to become resistant to a wide range of these insecticides. As a result, many of these insecticides are no longer effective at combating insect pests.

Furthermore, even compounds with limited mammalian toxicity, such as synthetic pyrethroids, may have significant toxicity toward non-targeted organisms such as birds and fish. The problem is particularly troublesome in light of the higher application rates and more frequent applications that often accompany the development of pest resistance. In such situations, a pesticide may cause increasing environmental damage as it becomes less and less effective for controlling pests.

These concerns, in combination with more stringent environmental standards, drive a worldwide effort to discover and develop improved insecticides. One proposed approach has been to use natural pathogens of insects as a means of combating insect pests. The natural pathogens are particularly suited as biological insecticides because they are generally quite selective, infecting only a limited number of closely related species. Accordingly, the pathogen's specificity for insects limits the environmental and health risks associated with chemical insecticides. In addition, these pathogens generally do not adversely affect beneficial arthropods, which in many cases are themselves natural predators of insects.

From an agricultural standpoint, the most important pathogens are bacteria, such as *Bacillus thringiensis* (B.t.), and baculoviruses, such as *Autographa californica* nuclear polyhedrosis viruses (AcNPV). Unfortunately, naturally occurring pathogens have limited utility as biological insecticides. The pathogens' limited host range and slow action often make them impractical for commercial purposes. Infected insects may not die for several days after infection, and continue to feed for much of that time. Thus, the use of this technology in actual insect control has been limited up to now.

Natural predators of insects such as spiders, wasps and scorpions have also been known for some time to contain toxins which paralyze insect pests. Due to technological limitations in the field, however, many of these toxins could not be purified in sufficient quantities to determine their potential commercial utility. Recent advances in molecular biology have made it possible to clone the genes which code for some of these toxins. These genes may now be used to create recombinant hosts which allow the purification of large quantities of insecticidal peptide. These genes may also be used to recombinantly alter insect pathogens, thereby increasing both their toxicity and their host range.

Moreover, because insects have shown an ability to become resistant to chemical insecticides, it is expected that they will similarly show an ability to become resistant to biological insecticides. Studies suggest that several biological agents could be introduced into insect pests simultaneously or in sequential applications. This would increase the toxicity of the insecticidal agents, while simultaneously reducing the chances that the insect pests will become resistant to the insecticidal cocktail.

Thus, it is apparent that it would be a significant advancement in the art to discover novel biological insect control agents that do not pose the environmental and health risks associated with chemical insecticides. It would be a further advancement in the art to provide such insect control agents which were selective for insects and which did not adversely affect humans or other animal or plant life. In that regard, it would be a significant advancement in the art to provide methods and compositions for controlling insects using naturally occurring insecticidal peptides.

SUMMARY OF THE INVENTION

The present invention relates to a family of insecticidally effective proteins isolated from the spider, Calisoga sp., characterized by their neurotoxic effect on insects pests. These proteins are exemplified herein by the peptides SEQ ID NO:1 (also at times designated herein as "peptide A"), SEQ ID NO:2 (also at times designated herein as "peptide B"), and SEQ ID NO:3 (also at times designated herein as "peptide C"), as well as the cDNA sequences for three of the peptides designated SEQ ID NO:5 (peptide A cDNA), SEQ ID NO:6 (peptide B cDNA) and SEQ ID NO:7 (peptide C cDNA). The characteristics of each of these peptides are more fully set forth below. When small quantities of these proteins are administered by injection into the abdomen of larvae of the tobacco budworm, the larvae are incapacitated by an excitatory paralysis.

This invention also relates to the cloning of these peptides using routine recombinant DNA technology. The cDNA sequences of peptides A, B, and C have been identified to date. The SEQ ID NO:5 (peptide A cDNA) encodes a precursor protein which is 80 amino acids in length. The first 41 amino acids encode a leader sequence which contains a putative signal sequence and propeptide, while the last 39 amino acids encode the mature toxin. The SEQ ID NO:6 (peptide B cDNA) and SEQ ID NO:7 (peptide C cDNA) cDNA sequences encode mature proteins which are 39 amino acids in length. The amino acid sequences encoded by the SEQ ID NO:6 (peptide B cDNA) and SEQ ID NO:7 (peptide C cDNA) cDNA sequences are nearly identical to the mature toxin encoded by SEQ ID NO:5 (peptide A cDNA) differing only at one or three amino acid positions, respectively. Each substitution is a result of a single nucleotide mutation.

In yet another aspect, the present invention teaches methods for modifying and improving the described peptides for use as insecticidal agents. A signal sequence and propeptide sequence, for example, may be useful for efficiently secreting the Calisoga peptides or targeting them to a specific cell or location in a cell. Signal sequences could, therefore, obviate the need for lengthy purification procedures and enhance the secretion and insecticidal efficacy of the Calisoga peptides.

Finally, this invention relates to the use of these peptides as agents for combating insect pests. Large quantities of these peptides may be obtained using known recombinant technology methods. The peptides can be engineered into an expression vector which is then inserted into either a prokaryotic host, such as *E. coli*, or a eukaryotic host, such as the insect cell line SF-9. The isolated protein may then be applied directly to the plant or animal sought to be protected from insect pests. The isolated protein may also be used to characterize the pharmacology of its target site by use in receptor binding assays, neurophysiological assays, or other appropriate test systems.

Alternatively, the peptides may be engineered into a natural pathogen of insects such as Bacillus or baculovirus. The recombinant pathogens can be utilized to transfer nucleic acids encoding the peptide directly into the insect pests. These recombinantly engineered pathogens will have significantly increased insecticidal efficacy in comparison with the parental wild-type pathogens.

These and other objects and advantages of the invention will become apparent upon reading the following detailed description and appended claims, and upon reference to the accompanying drawings.

DETAILED DESCRIPTION OF THE DRAWINGS

FIG. 1 is a chromatogram illustrating the results of fractionating whole *Calisoga venom* by reversed phase chromatography. The peptide SEQ ID NO:1 (peptide A) eluted between 30–34 minutes, peptide SEQ ID NO:2 (peptide B) eluted between 34–36 minutes, and peptide SEQ ID NO:3 (peptide C) eluted between 36–37 minutes.

FIG. 2 is a chromatogram from cation-exchange chromatography performed on pooled fractions 14 and 15, which eluted between 30 and 34 minutes, from the reversed-phase chromatography plotted in FIG. 1, containing SEQ ID NO:1 (peptide A). Fraction 2, which eluted between 34 and 38 minutes, contains peptide SEQ ID NO:1 (peptide A).

FIG. 3 is a chromatogram from cation-exchange chromatography performed on fraction 16, which eluted between 34 and 36 minutes, from the reversed-phase chromatography illustrated in FIG. 1, containing SEQ ID NO:2 (peptide B). Fraction 2 contains peptide SEQ ID NO:2 (peptide B).

FIG. 4 is a chromatogram from cation-exchange chromatography performed on fraction 17, which eluted between 36 and 37 minutes, from the reversed-phase chromatography illustrated in FIG. 1, containing SEQ ID NO:3 (peptide C). Fraction 2 contains peptide SEQ ID NO:3 (peptide C).

DETAILED DESCRIPTION OF THE INVENTION

As discussed above, the present invention is related to peptides isolated from spider venom which display insecticidal characteristics. More particularly, the present invention relates to a family of insecticidally effective peptides isolated from the spider Calisoga sp., characterized by their neurotoxic effect on selected insect pests. For the purposes of this application, the term "insecticidally effective" shall be defined as effective in incapacitating by excitatory paralysis the larvae of the tobacco budworm under the conditions set forth herein.

As mentioned above, these proteins are exemplified herein by the peptides SEQ ID NO:1 (peptide A), SEQ ID NO:2 (peptide B), and SEQ ID NO:3 (peptide C), as well as the cDNA sequences for three of the peptides designated SEQ ID NO:5 (peptide A cDNA), SEQ ID NO:6 (peptide B cDNA) and SEQ ID NO:7 (peptide C cDNA). The specification describes how these peptides may be expressed by recombinant DNA methods. In addition, it is possible, by known techniques, to transform or transfect expression vectors containing a toxin cDNA sequence into a host cell or organism.

Accordingly, the present invention provides naturally occurring peptides for use as insecticides. The naturally occurring peptides may be used in a variety of ways to control insects, or to study the effects of such peptides on insects.

EXPERIMENTAL METHODS AND CHARACTERIZATION

The primary operative techniques and terms used in this specification are well known in the art. Nevertheless, in order to provide a clear understanding of the full scope of the present invention, reference is made to the following experimental methods and characterization techniques which may be used to practice the invention.

VENOM PRODUCTION

Spiders were collected from known wild populations and identified as Calisoga sp. (Araneae: Nemesiidae). Venom was produced by an electrical milking technique which avoids contamination of the venom with digestive enzymes and other regurgitated substances.

BIOASSAY

Whole venom was isolated by known techniques from the spider, Calisoga. The whole venom, or peptides purified therefrom, were dissolved in sterile buffered physiological saline. For testing and characterization purposes, venom and toxins were administered by injection into the abdomen of fifth instar larvae of the tobacco budworm (TBW), *Heliothis virescens*. Control larvae were injected with an equal volume of saline. After treatment, the insects were placed individually in Petri dishes, with food, and observed.

Insects that could not right themselves within thirty seconds of being placed on their backs or side were considered paralyzed. Fifty percent paralytic dose ($PD_{50}$) values were calculated by probit regression (see Example 2). Raymond, M., *Ser. Ent. med et Parasitol*, 22(2), 117–121 (1985).

PROTEIN PURIFICATION

Peptides from Calisoga spider venom were isolated using methods known in the art. Briefly, whole venom was first fractionated by reversed-phase chromatography. Fractions were collected by monitoring ultraviolet absorbance. Based on biological activity, three peaks were identified as containing the peptides of interest.

The biologically active fractions were further purified by cation-exchange chromatography. Fractions again were collected by monitoring UV absorbance and were bioassayed. The biologically active fractions were then desalted by reversed-phase chromatography. The resulting fractions contained substantially pure peptides SEQ ID NO:1 (peptide A), SEQ ID NO:2 (peptide B) and SEQ ID NO:3 (peptide C) (see Example 1). The observed molecular masses for purified peptides SEQ ID NO:1 (peptide A), SEQ ID NO:2 (peptide B) and SEQ ID NO:3 (peptide C) are 4304.01, 4287.89 and 4289.64, respectively.

ANTIBODIES

Within the scope of this invention are included antibodies directed towards peptides SEQ ID NO:1 (peptide A), SEQ ID NO:2 (peptide B), and SEQ ID NO:3 (peptide C) and, by extension, to similar peptides. Antibodies are proteins that are generated in animals and said to recognize or bind to a specific protein. When studying the insect toxins of this invention, it would be useful to be able to monitor the toxins' quantity, location and association with other proteins. Techniques such as Western blots, immuno-precipitation assays, and immunohistochemical assays cannot be performed without employing an antibody that specifically recognizes the peptide of interest.

In addition, antibodies can be used, by methods well known in the art, to purify and subsequently clone the proteins to which these toxins bind. This may be done by screening expression libraries, for example. Alternatively, these proteins may be purified by immobilizing the antibody to a solid support and by employing immunoaffinity chromatography.

Antibodies can be produced by a variety of methods well known in the art. Generally, antibodies are generated by immunizing a foreign animal (typically, rabbits or mice) with purified proteins. Insect toxins which are purified from whole spider venom, recombinantly expressed, or synthesized would be suitable for antibody production. The proteins induce an immune response in the animal, resulting in the production of many antibodies that recognize the protein. The sera of these animals contain polyclonal antibodies, which are a mixture of many antibodies that recognize the protein or a fragment or derivative thereof.

Alternatively, a single antibody, referred to as a monoclonal antibody, may be produced by hybridoma cloning technology well known in the art. See, Kennett, R. H. et al. *Monoclonal Antibodies, Hybridomas: A New Dimension in Biological Analyses*. Plenum Press, New York, 1982. Briefly, the animal is immunized and the splenocytes of the animals are isolated and immortalized by fusing them with a suitable myeloma cell line. The cells are cloned by limited dilution. The cell lines that produce suitable monoclonal antibodies are kept and the remaining cell lines are discarded.

Thus, it is possible to produce antibodies to the peptides of this invention in order to facilitate further characterization, research, and development related to the use of the insecticidal toxins of interest.

cDNA ISOLATION AND CHARACTERIZATION

The SEQ ID NO:5 (peptide A cDNA) cDNA was isolated by methods well known to those in the art (see Example 3). Generally, the N-terminal sequence of peptide SEQ ID NO:1 (peptide A) was determined by chemical sequencing. Based on the genetic code and available codon usage data for spiders, degenerate oligonucleotides complementary to the nucleic acid sequence encoding the first 8 amino acids of the protein were synthesized. The oligonucleotides were used in selective amplification of the cDNA sequence encoding mature toxin peptide A (SEQ ID NO:1, which is also the sequence beginning with amino acid residue 1 of SEQ ID NO:5) by polymerase chain reaction techniques. The resulting products were confirmed by DNA sequencing. The upstream sequence was obtained by 5' rapid amplification of cDNA ends (5'-RACE). The resulting upstream cDNA fragment was ligated to the cDNA fragment encoding the mature "A" peptide with a Kpn1 restriction site.

The isolated cDNA was 397 nucleotides in length. This includes both the 5' and 3' untranslated regions flanking the open reading frame of the SEQ ID NO:5 (peptide A cDNA) cDNA. The encoded precursor protein is 80 amino acids in length. The first 41 amino acids (−41 through −1) of the precursor protein make up the leader sequence. This region contains a highly hydrophobic region of about 21 amino acid residues which likely functions as a secretion signal in the spider. The remaining precursor amino acids encode an acidic propeptide. It is believed that this "prepropeptide" is proteolytically cleaved to yield the mature protein product (amino acids 1 through 39). Based on the amino acid sequence derived from the cDNA sequence, the calculated molecular mass of the mature toxin encoded by the SEQ ID NO:5 (peptide A cDNA) cDNA, subtracting 8.08 amu for the probable loss of eight hydrogen atoms due to the presumed presence of four disulfide bonds, is 4303.5. This number correlates well with the observed mass obtained from purified peptide SEQ ID NO:1 (peptide A), suggesting that peptide SEQ ID NO:1 (peptide A) is likely encoded by the SEQ ID NO:5 (peptide A cDNA) cDNA.

The cDNA sequences corresponding to mature peptides SEQ ID NO:6 (peptide B cDNA) and SEQ ID NO:7 (peptide C cDNA) were similarly isolated except no upstream sequences were obtained. However, because of the high similarity among peptides A, B, and C, it is likely that these peptides are derived from highly related precursor peptides. A comparison of the mature peptide SEQ ID NO:5 (peptide A cDNA), SEQ ID NO:6 (peptide B cDNA) and SEQ ID NO:7 (peptide C cDNA) reveals that the clones are nearly identical at the nucleic acid level. The mature proteins encoded by SEQ ID NO:6 (peptide B cDNA) and SEQ ID NO:5 (peptide A cDNA) are identical except for an amino acid substitution (Phe instead of Tyr) at residue 26. Similarly, the mature proteins encoded by SEQ ID NO:7 (peptide C cDNA) and SEQ ID NO:5 (peptide A cDNA) are identical except for three amino acid substitutions at residues 18 (Ser instead of Asn), 21 (Ile instead of Thr), and 27 (Leu instead of Ile). Each amino acid substitution is the result of a single nucleotide mutation.

Based on the amino acid sequence derived from the cDNA sequences, the calculated molecular masses for the mature toxins encoded by the SEQ ID NO:6 (peptide B cDNA) and SEQ ID NO:7 (peptide C cDNA) cDNA sequences, subtracting 8.08 amu for the probable loss of eight hydrogen atoms due to the presumed presence of four disulfide bonds, are 4287.5 and 4288.52, respectively. These calculated molecular masses correlate well with the observed masses obtained from purified peptides SEQ ID NO:2 (peptide B) and SEQ ID NO:3 (peptide C), suggesting that these peptides are likely encoded by the SEQ ID NO:6 (peptide B cDNA) and SEQ ID NO:7 (peptide C cDNA) cDNA sequences.

PROTEIN MODIFICATIONS

Protein modifications can be subdivided into four general categories: chemical processing, additions, substitutions and deletions. These general groups apply to both the nucleic acid and amino acid sequences of the protein. While protein modifications may occur naturally, most often protein modifications are deliberately engineered into the nucleic acid sequence that codes for the protein. Protein modification techniques such as site-directed mutagenesis are well known in the art and in many cases are commercially available as kits complete with instructions from, example, Amersham and Bethesda Research Laboratories.

Chemical processing generally occurs after protein translation, and includes modifications such as amidation, glycosylation, palmitoylation, and isomerization. Such processing events may be necessary for the stability and optimal activity of toxins (Heck et al., Science, 266: 1065–1068, 1994).

A protein modification may occur through an addition. Additions as defined herein are modifications made to the nucleic acid or amino acid sequence which produce a protein containing at least one amino acid more than the primary amino acid sequence of the protein without significantly altering the function of the toxin. Naturally occurring nucleic acid additions in the coding region of the protein often severely impair the protein's function by causing a shift in the reading frame. From the point of the nucleotide addition, the amino acid sequence is entirely different than the primary amino acid sequence of the protein. It is possible, however, to have an addition within the coding region of the protein which does not change the reading frame of the protein. Nucleotide additions in the 5' or 3' untranslated region of the gene usually do not affect protein function.

As mentioned above, additions are usually deliberately engineered into the protein. In the present invention, for example, the mature protein lacks an initiator methionine which may be preferred for the efficient translation of the protein. Thus, the addition of a methionine to the amino terminus of the mature protein, as well as additions of other amino acids and nucleotides which facilitate the expression of the protein such as stop codons and ribosomal binding sites are included within the scope of this invention.

It is also understood that the addition of a signal sequence or signal peptide is included within the scope of this invention. Signal sequences direct protein transport to a particular location within the cell or organism. Alternatively, signal sequences may cause the protein to be secreted.

Comparison of all known signal peptides reveals that they are approximately 15–30 residues in length. Within the signal peptide there is a 7–13 residue stretch that constitutes a hydrophobic region (h-region). The h-region is rich in Ala, Met, Val, Ile, Phe and Trp, and occasionally contains Pro, Gly, Ser or Thr residues. von Heijne, G., J. Mol. Biol. 184, 99–105 (1983). This sequence homology is shared from bacteria to higher eukaryotes, suggesting that the localization machinery is highly conserved. Proteins from one organism can be translocated and correctly processed by the localization machinery of several other organisms. Mueller et al., J. Biol. Chem., 257, 11860–11863 (1982). Conversely, recombinant proteins comprising a signal peptide from one organism and a protein from a different organism are also properly localized. Yost et al. (1983); Jabbar & Nayak, Mol. Cell. Biol., 7, 1476–1485 (1987). Studies suggest that signal sequences form their functional conformation independent of the remaining protein sequence which explains why signal sequences are readily interchangeable between different proteins and different species.

In fact, studies performed using the scorpion peptide, AaIT, in baculovirus demonstrate that the addition of a signal sequence from one species to an insect toxin from another species is expected to succeed. The AaIT peptide was fused with the signal sequence from bombyxin, a secretory peptide from the silkworm Bombyx mori, and shown to secrete a functional AaIT peptide that was toxic to insects. McCutchen, B. F. et al., Bio/Technology 9, 848–852 (1991).

Finally, a secretory signal peptide may also greatly facilitate the purification of a peptide in an expression system by having the protein product secreted into the culture media rather than being retained by the host cell. In many instances the proteins are sufficiently pure in the media such that further purification is not required. This is particularly true for small proteins which are stable under a broad range of conditions.

Signal peptides for many prokaryotes, as well as eukaryotes and viruses are well characterized and documented in the literature. Thus, using basic recombinant DNA technology, such as PCR or synthetic oligonucleotides, a recombinant protein containing a signal peptide at its amino terminus can be easily engineered.

It is also understood that the addition of an antigenic epitope is included within the scope of the present invention. An epitope is a small, usually 6–20 amino acid residues, antigenic peptide for which a unique and specific antibody exists. Thus, by recombinantly engineering an antigenic epitope, the scientist is guaranteed a specific and effective antibody that will recognize the specific peptide. One such antigenic epitope is the c-myc epitope which has been recombinantly engineered into many proteins without any deleterious effect on function. Several other epitopes have been well documented in the literature and are commercially available along with the antibodies that recognize them. Like the signal peptides, a recombinant protein containing an epitope can be engineered using common recombinant DNA technology. Unlike the signal peptide, however, the antigenic epitope may be engineered at the amino terminus or the carboxy terminus of the protein.

Protein modifications which occur through substitutions are also included within the scope of the invention. Substitutions as defined herein are modifications made to the nucleic acid or amino acid sequence of the protein, producing a protein which contains a different amino acid sequence than the primary protein without significantly altering the function of the toxin. Like additions, substitutions may be natural or artificial. It is well known in the art that amino acid substitutions may be made without significantly altering the protein's function. This is particularly true when the modification is the substitution of an amino acid for a "conserved" amino acid. Conserved amino acids are natural or synthetic amino acids which because of size, charge, polarity and conformation can be substituted without significantly affecting the structure and function of the protein. Frequently, many amino acids may be substituted by conservative amino acids without deleteriously affecting the protein's function.

Whether an amino acid can be substituted at all, or whether it can only be substituted by a conserved amino acid is best determined by comparing the specific peptide of interest with other spider insect toxins. Amino acids that are identical in all the members of a protein family usually cannot be substituted. This is often the case with cystine residues which are critical for the formation of the protein's secondary structure. Amino acids which are conserved can usually be substituted by other conserved amino acids without significantly affecting the protein's function.

Finally, amino acids which are not conserved within a family can usually be freely substituted.

In general, the non-polar amino acids Gly, Ala, Val, lie and Leu; the non-polar aromatic amino acids Phe, Trp and Tyr; the neutral polar amino acids Ser, Thr, Cys, Gin, Asn and Met; the negatively charged amino acids Lys, Arg and His; the positively charged amino acids Asp and Glu, represent groups of conservative amino acids. This list is not exhaustive. For example, it is well known that Ala, Gly, Ser and sometimes Cys can substitute for each other even though they belong to different groups.

Conservative amino acid substitutions are not limited to naturally occurring amino acids, but also include synthetic amino acids. Commonly used synthetic amino acids are ω amino acids of various chain lengths and cyclohexyl alanine which are neutral non-polar analogs; citulline and methionine sulfoxide which are neutral non-polar analogs, phenylglycine which is an aromatic neutral analog; cysteic acid which is a positively charged analog and ornithine which is a negatively charged amino acid analog. Like the naturally occurring amino acids, this list is not exhaustive, but merely exemplary of the substitutions that are well known in the art.

Finally, protein modifications may occur through deletions. Deletions as defined herein are modifications made to the nucleic acid or amino acid sequence of the protein which produce a protein containing at least one amino acid less than the primary amino acid sequence of the protein, without significantly altering the function of the toxin. Like additions, naturally occurring deletions within the coding region of the protein usually severely impair the function of the protein, while deletions in the 5' and 3' untranslated region do not affect the function of the protein.

Deliberate deletions, however, may be required or useful for the expression of the protein in a foreign organism. For example, the cDNA sequences of SEQ ID NO:5 (peptide A cDNA), SEQ ID NO:6 (peptide B cDNA) and SEQ ID NO:7 (peptide C cDNA) code for both the leader sequence and the mature protein. In the spider the leader sequence is most likely removed by proteolysis as the prepropeptide secreted. A deletion which removes the leader sequence from the precursor protein will, therefore, yield a functional mature protein similar to that secreted by the spider. Accordingly, deletion of the Calisoga peptide's leader sequences, as well as deletions which facilitate the expression of the peptides are to be included within the scope of the invention.

RECOMBINANT EXPRESSION

Once the cDNA has been recombinantly modified to express a protein suited for a particular need, the cDNA, including all modifications, is subcloned into an expression vector. In general, expression vectors are like plasmids which additionally contain a promoter, a termination signal and sometimes a selectable marker. Any expression vector containing a prokaryotic, eukaryotic or viral promoter and a termination signal is included within the scope of the invention.

A promoter is a nucleic acid sequence, generally engineered 5' to the cDNA, which recruits and directs the transcription of RNA using the cDNA as a template. From this transcribed RNA message, the cell can assemble the protein which is encoded by the cDNA through a process known as translation.

Promoters can generally be classified as constitutive, inducible, or tissue specific. A constitutive promoter is a promoter which is not regulated to a significant extent by any cellular factors and continually directs the transcription of the RNA. These promoters are used when large quantities of protein are desired. The cytomegalovirus promoter and the Rous Sarcoma virus promoters are examples of constitutive eukaryotic promoters. The int promoter of bacteriophage 1 and the bla promoter of β-lactamase are examples of constitutive prokaryotic promoters.

Included in this group are promoters which are characterized as early or late promoters. These promoters are usually viral promoters which are activated to high levels either early or late in viral replication. The baculovirus p10 and polyhedrin promoters are examples of late promoters.

Inducible promoters are promoters that are induced or repressed by certain factors. These promoters allow regulation of the amount of protein produced, and the timing of such production. Examples of inducible promoters are the eukaryotic metallothionine promoter which is induced by increased levels of heavy metals and the prokaryotic lacZ promoter which is induced in response to isopropyl β-D-thiogalacto-pyranoside (IPTG).

Finally, tissue specific promoters are promoters which only function in a particular cell type. These promoters are usually used when expression of the protein in all cell types is harmful to the organism. An example of a mammalian tissue specific promoter is the skeletal muscle creatine kinase promoter.

An expression vector also requires a termination signal. The termination signal is usually engineered 3' to the protein of interest. In higher eukaryotes, for example, the expression vector must contain a polyadenylation signal in order for the transcript to be translated into a protein. A termination signal like the adenovirus polyadenylation signal and the baculovirus polyhedrin polyadenylation signal may be used. Alternatively, a peptide's own polyadenylation signal may serve as an efficient termination signal.

In most instances, the expression vector also requires a selectable marker which allows for the identification of cells which have actively incorporated the expression vector. These selectable markers are genes whose protein product confers resistance to an antibiotic or other chemical. Thus, cells that are capable of growing in the presence or absence of a certain chemical are known to contain the expression vector. Examples of selectable markers are the β-lactamase gene which confers resistance to ampicillin in prokaryotes and the neomycin gene which confers resistance to G-418 in eukaryotic cells. An expression vector is not limited to one selectable marker and, in fact, most expression vectors contain multiple selectable markers.

In short, the availability and knowledge of prokaryotic and eukaryotic promoters, termination signals and selectable markers is well known in the art. In fact, many types of expression vectors for bacterial, yeast, mammalian and viral expression systems are commercially available.

RECOMBINANT HOSTS

The desired expression vector, including the cDNA, is then transformed or transfected into the host cell or organism. Both transformation and transfection refer to the incorporation of the expression vector into a host by methods such as electroporation or calcium phosphate treatment which are well known in the art. Like plasmids, expression vectors may remain episomal or be incorporated as part of the host's genome. Incorporation into the host genome can be accomplished by either random integration or homologous recombination. Random integration results in the insertion of multiple genes in unknown locations of the host's genome, while homologous recombination results in the insertion of one copy of the gene in a known location of the host's genome. The above techniques are expected to be useful for the expression of the peptides of this invention and are included within the scope of the invention.

Recombinant hosts are chosen based on the goals to be achieved. For the purposes of expressing an insecticidally effective protein there are two general types of hosts which are particularly useful: hosts that are useful for isolating large quantities of recombinant proteins, and hosts that infect insect pests.

Bacteria, particularly *E. coli*, are still the most commonly used host for the isolation of large quantities of recombinant proteins. A recombinant bacterial host expressing an insect toxin, therefore, is expected to be a useful technique for isolating the insect toxins of the present invention for use as insecticides. The toxin may be fused to a signal peptide as described above or expressed as a mature protein. Bacterial overexpression systems are well known in the art and are commercially available.

The toxins expressed in a bacterial overexpression system, however, will not contain post-translational modifications. Therefore, baculovirus infected insects or insect cell lines are frequently employed to isolate large quantities of post-translationally modified proteins. A wide variety of prokaryotic and eukaryotic proteins have been successfully expressed in baculovirus. Luckow, V. and Summers, *M. Bio/Technology* 6, 47–55 (1988); Summers, M. D. and Smith, G. E. *Texas Agricultural Experimental Station Bulletin,* 1555, 1–56 (1987).

As in bacterial hosts, recombinant baculoviruses may express proteins as either fusion or mature proteins. Expression of foreign genes has been known to yield as much as 500 mg/liter of protein. Because insect cells are eukaryotic, the recombinant proteins produced using baculovirus infected insect cells are very similar to the native proteins. Studies have shown that recombinant proteins expressed by a baculovirus vector may be secreted, localized to the nucleus, localized to the cell surface, disulfide-linked, proteolytically cleaved, phosphorylated, N-glycosylated, O-glycosylated, myristylated or palmitylated. Luckow, V. and Summers, *M., Bio/Technology* 6, 47–55 (1988).

The recombinant peptide isolated from these hosts may be applied directly to the plants or animals sought to be protected from the insect pests. As discussed later, the recombinant virus itself may be used as a pest control agent.

Alternatively, the recombinant peptide will be used to study the physiological mechanism which leads to the paralysis of insect pests. Given the mechanism of action of other spider toxins, it is likely that the peptides of interest herein act by altering the function of ion channels. Moreover, the art strongly suggests that these toxins are highly selective for insect pests displaying negligible mammalian toxicity. This is true despite the fact that analogous ion channels and other target sites are abundantly present in mammals. Some of these targets, notably voltage-sensitive sodium channels, are important targets for chemical insecticides. Therefore, peptides, such as the toxins of this invention, may be used to help elucidate and characterize the differences between the insect and vertebrate forms of these target sites. This information can then be used in chemical design studies aimed at developing chemical insecticides which are highly selective for insect pests.

Pathogens infecting insects represent a second class of recombinant hosts useful for the expression of the subject peptides. From an agricultural standpoint, bacteria and baculoviruses are the most promising pathogen candidates although pathogenic fungi might also be used for this purpose.

Certain bacteria pathogenic to insects, especially *Bacillus thuringiensis* (B.t.), have been used to control a variety of insect pests. Unfortunately, naturally occurring pathogens often have limited utility as biological insecticides due to limitations in delivery, toxicity and speed of action. Current work, however, has demonstrated that B.t. may be engineered to produce a recombinant bacterium which overcomes some of the limitations of the wild-type B.t. Most notably, the B.t. delta-endotoxin gene has been engineered into bacterial pathogens to produce hybrid hosts which display superior insecticidal properties. Similarly, the production of recombinantly engineered bacterial or fungal pathogens which express the toxins of this invention are thought to be useful and thus included within the scope of the invention.

Wild-type baculoviruses are also natural regulators of many different types of insects pests, including *Heliothis virescens* (tobacco budworm), *Orgyia pseudotsugata* (Douglas fir tussock moth) and *Laspeyresia pomonella* (codling moth). See Gröner, A., 1986, Specificity and Safety of Baculovirus. Vol I *Biological Properties and Molecular Biology,* Granados, R. R. and Federici, B. A. eds. CRC Press, Inc. Boca Raton, Fla. Baculoviruses, such as *Autographa californica* nuclear polyhedrosis virus, produce post-infection viral progeny: extracellular viral particles and occluded viral particles. The occluded viral particles are important because they provide a means for horizontal and vertical transmission. After infected insect pests die, millions of viral particles are left behind protected by the viral occlusion. Thus, when insect pests feed on contaminated plants, they ingest the occlusion bodies. The occlusion bodies dissolve in the alkaline environment of the insect gut releasing the viral particles which infect and replicate in the insect's midgut tissue. Secondary infection within a host is spread by extracellular, non-occluded viral particles.

Unfortunately, insects infected by baculoviruses may take a week or more to die and continue to feed for much of that time, making the commercial use of wild-type baculovirus commercially infeasible. It has been shown, however, that baculoviruses, such as the *Autographa californica* nuclear polyhedrosis virus, can be recombinantly engineered to express an insecticidal toxin, thus accelerating their pathogenic effects. McCutchen, B. F. et al., *Bio/Technology,* 9, 848–852 (1991); Tomalski et al., *Nature,* 352, 82–85 (1991); Stewart et al., *Nature,* 352, 85–88 (1991). A recombinant vector, Pacuw2(B).AaIT, was constructed containing a polyhedrin gene driven by the polyhedrin promoter and the AaIT insect toxin driven by the p10 promoter. The resulting recombinant baculovirus was orally infective under normal conditions. Furthermore, the AaIT toxin was secreted in the course of infection and caused paralysis of both *Manduca sexta* larvae, an unnatural host for the virus, and *Heliothis virescens* larvae, a natural host.

Using basic recombinant technology well known in the art, it is expected that the peptides of the present invention could similarly be recombinantly engineered to produce a recombinant baculovirus which would display increased host range and toxicity. (see Example 9).

Figure 4:
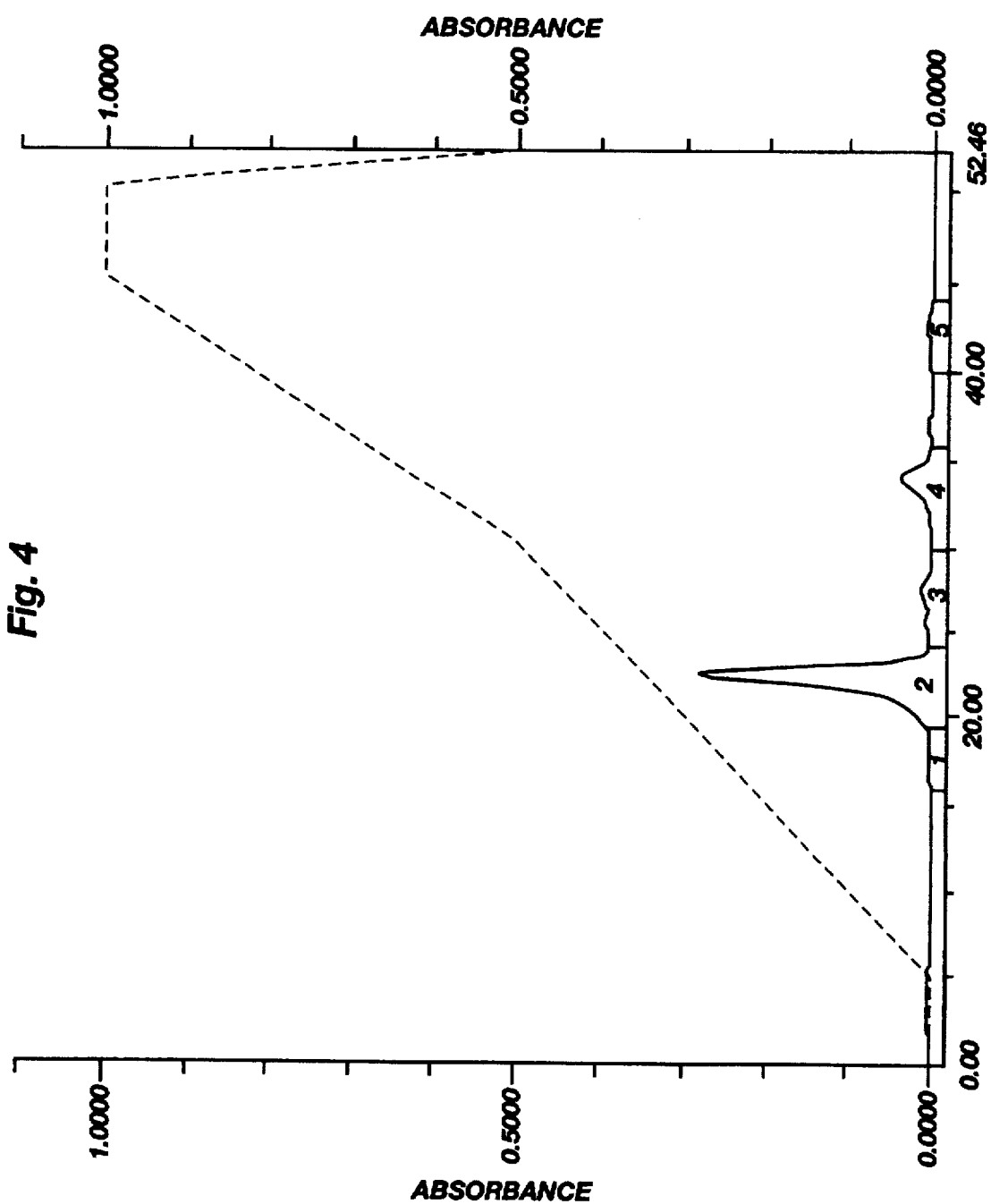

Recombinant baculoviruses expressing the toxins of this invention, like current insecticides, could then be administered to the crops sought to be protected from insect pests. The release of recombinant baculoviruses into the environment is expected to be a safe and effective means of controlling insect pests. First, naturally occurring insecticidal peptides are highly selective. In addition, baculoviruses do not infect mammals and are highly selective within an insect group. Therefore, by carefully selecting the baculovirus host and insecticidal peptide, it is possible to engineer recombinant baculoviruses which are highly selective for the target insect pest while simultaneously reducing the impact on non-targeted organisms, including beneficial insects. Second, recombinant baculoviruses, in the absence of strong selective pressure, are likely to revert back to the wild-type after a short time of being exposed to environmental pressures. Thus, the relatively short life of the recombinant baculoviruses further reduces the risk to non-targeted species.

The quantity and frequency of recombinant baculovirus application will necessarily depend on such things as the particular crop being protected, the insect pest and the climate. Accordingly, the quantity and frequency of recombinant baculovirus application is best determined empirically.

EXAMPLES

The following examples are given to illustrate various embodiments which have been made or may be made in accordance with the present invention. These examples are given by way of example only, and it is to be understood that the following examples are not comprehensive or exhaustive.

EXAMPLE 1

Bioassays

Whole venom from a spider, Calisoga sp. (Aranae: Nemesiidae), was dissolved in the desired volume of sterile, buffered physiological saline. Samples were administered by injection into the abdomen of the fifth instar larvae of the tobacco budworm, *Heliothis virescens*, as previously described. Control larvae were injected with equal volumes of saline.

When whole Calisoga venom was injected into *H. virescens* larvae, paralysis developed gradually and was preceded by a period of pronounced muscle spasms in the body wall. These spasms began within 15–30 minutes of injection and gradually increased in intensity until the larvae were completely incapacitated. Tremoring sometimes persisted for more than 48 hours after injection; eventually the tremors gave way to a generalized, flaccid paralysis. Affected larvae fed very little or not at all. Control larvae were unaffected.

TABLE 1

Calisoga sp. whole venom screening in last instar larvae of the tobacco budworm (TBW), *Heliothis virescens*.

| Dose (μl/larva) | Paralyzed/total 24 hr | Paralyzed/total 48 hr |
|---|---|---|
| 0.3 | 4/6 | 4/6 |
| 0.03 | 0/6,4 FI | 2/6,2 FI |
| Control | 0/6 | 0/6 |

(FI = feeding inhibited but not paralyzed)

EXAMPLE 2

Purification of Peptide SEQ ID NO:1 (peptide A)

Whole Calisoga venom was fractionated by reversed phase chromatography. The whole venom (200 microliters (μl)) was diluted with 5 ml of 15% acetonitrile/0.1% TFA and the sample was chromatographed in three aliquots on a Vydac C-18 column (300 Å, 10×250 mm) equilibrated in the same buffer. Five minutes after injection of the sample the column was developed with a 37 minute linear gradient from 15–33.5% acetonitrile/0.1% TFA, followed by a 10 minute linear gradient to 100% acetonitrile/0.1% TFA. The results are illustrated in FIG. 1. The flow rate was 3.5 ml/minute and the effluent was monitored at 220 nm. Fractions were collected as noted on the chromatogram. Like fractions were pooled and lyophilized. SEQ ID NO:1 (peptide A) eluted between 30–34 minutes. A small portion of the pooled, lyophilized fraction was used to confirm biological activity; the remaining material was dissolved in 2.5 ml 50 mM NaOAc, pH 4.0 and fractionated by cation-exchange chromatography.

Cation-exchange chromatography was performed on a HEMA-IEC BIO SB column (10 μm, 4.6×150 mm, from Alltech Associates, Deerfield, Ill. 60015). The solution containing SEQ ID NO:1 (peptide A) from the reversed-phase chromatography was loaded onto the HEMA-IEC BIO SB column equilibrated in the same buffer. After 5 minutes, the column was developed with a 25 minute linear gradient from 0–0.5M NaCl in 50 mM sodium acetate buffer, pH 4.0, followed by a 15 minute linear gradient from 0.5–1M NaCl in 50 mM sodium acetate buffer, pH 4.0. The results are illustrated in FIG. 2. Elution was at 1 ml/minute and the effluent was monitored at 280 nm. Fractions were collected as noted on the chromatogram.

The major peak of material from the cation-exchange chromatography of SEQ ID NO:1 (peptide A) eluted between 34 and 38 minutes. This fraction (4 ml) was desalted on a Vydac C-18 reversed-phase column (4.6×250 mm, 300 Å) equilibrated in 20% acetonitrile/0.1% TFA. After 14 minutes, the column was developed with a 60 minute linear gradient from 20–50% acetonitrile/0.1% TFA, followed by a 5 minute linear gradient from 50–100% acetonitrile/0.1% TFA. Elution was at a flow rate of 1.0 ml/minute and the effluent was monitored at 220 nm. A single peak, eluting between 24 and 30 minutes, was lyophilized to give purified SEQ ID NO:1 (peptide A).

The observed mass of SEQ ID NO:1 (peptide A), as determined by mass spectral analysis performed by electrospray ionization at the Biotechnology Research Institute, Quebec, Canada, was 4304.01. The $PD_{50}$ of peptide SEQ ID NO:1 (peptide A) in TBW larvae was 2.37 μg/g with the 95% confidence interval ranging from 1.70–3.22 μg/g.

EXAMPLE 3

Purification of Peptide SEQ ID NO:2 (peptide B)

SEQ ID NO:2 (peptide B) was isolated by essentially the same method employed for the purification of peptide A described in Example 2. SEQ ID NO:2 (peptide B) eluted from the initial reversed-phase column between 34 and 36 minutes (see FIG. 1), and from the cation-exchange column between 25–30 minutes (see FIG. 3). SEQ ID NO:2 (peptide B) was then desalted like peptide A except that SEQ ID NO:2 (peptide B) eluted from the desalting column between 26–30 minutes. The observed mass of SEQ ID NO:2 (peptide B) was 4287.89. The $PD_{50}$ of peptide SEQ ID NO:2 (peptide B) in TBW larvae was 3.7 μg/g with the 95% confidence interval ranging from 1.72–8.0 μg/g.

EXAMPLE 4

Purification of Peptide SEQ ID NO:3 (peptide C)

SEQ ID NO:3 (peptide C) was isolated by essentially the same method employed for the purification of peptide A described in Example 1. SEQ ID NO:3 (peptide C) eluted from the initial reversed-phase column between 36 and 37 minutes (see FIG. 1), and from the cation-exchange column between 19–24 minutes (see FIG. 4). SEQ ID NO:3 (peptide C) was then desalted like peptide A except that SEQ ID NO:3 (peptide C) eluted from the desalting column between 26–30 minutes. The observed mass of SEQ ID NO:3 (peptide C) was 4289.64.

EXAMPLE 5

N-terminal Amino Acid Sequencing of Peptide SEQ ID NO:1 (peptide A)

N-terminal amino acid sequence analysis of the reduced, derivatized SEQ ID NO:1 (peptide A) peptide was performed at the Biotechnology Center of Utah State University. The sequence, which lacked one amino acid residue at the carboxy terminus, is shown below:

Cys Ile Ser Ala Arg Tyr Pro Cys Ser Asn Ser Lys Asp Cys Cys Ser Gly Asn Cys Gly Thr Phe Trp Thr Cys Tyr Ile Arg Lys Asp Pro Cys Ser Lys Glu Cys Leu Ala

The calculated molecular mass of this peptide is 4242.53.

EXAMPLE 6

Degenerate Oligonucleotide Synthesis

Based on the genetic code and available codon usage data for spiders, degenerate oligonucleotides complementary to the nucleic acid sequence which coded for the first 8 amino acids of the peptide of Example 5 were synthesized. The nucleic acid sequence of the degenerate oligonucleotides (SEQ ID NO:4) synthesized is shown below:

ATG ATW WSI GCY MGN TAY CCM TG where, A=adenine, T=thymidine, C=cytosine, G=guanine, W=A or T, S=C or G, I=inosine, Y=C or T, M=A or C, and N=A or G or T or C. SEQ ID NO:4 was used to selectively amplify the SEQ ID NO:5 (peptide A cDNA) cDNA as described in Example 7.

EXAMPLE 7

Isolation of the SEQ ID NO:5 (peptide A cDNA) cDNA

Spiders were anesthetized and the venom glands were removed. Total RNA was isolated by methods well known in the art. Briefly, the venom glands were homogenized in guanidinium thiocyanate. The homogenized tissue was then extracted with water-equilibrated phenol and chloroform until the interphase between the aqueous and organic phase was clear. The aqueous layer was precipitated with ethanol and the total RNA was recovered by centrifugation. Polyadenylated RNA (mRNA) was isolated using oligo d(T) cellulose chromatography kits purchased from Pharmacia.

Thereafter, fifty nanograms of mRNA was used as a template for the synthesis of cDNA. An oligonucleotide containing a string of 15 thymidine residues and additionally containing a Not I endonuclease recognition signal (hereafter $d(T)_{15}$) was allowed to hybridize to the mRNA. The cDNA was synthesized by Moloney murine leukemia virus reverse transcriptase under the conditions prescribed by the manufacturer, Bethesda Research Laboratories (BRL).

Selective amplification of the SEQ ID NO:5 (peptide A cDNA) cDNA was achieved by the PCR-RACE technique described by Frohman using the oligonucleotides $d(T)_{15}$ and SEQ ID NO:4 described in Example 6. Frohman, M. A., *PCR protocols*, ed. Innis et al., Academic Press, San Diego, Calif., (1990). The PCR-RACE was performed using one-fourth of the cDNA obtained in the previous step; 2 μM final of SEQ ID NO:4 and $d(T)_{15}$; 100 μM final of each deoxy- nucleotide triphosphate; and 4 units of AmpliTaq DNA polymerase purchased from Perkin Elmer.

Initially two cycles of the polymerase chain reaction were carried out by a denaturation step at 94° C. for 2 min., followed by a primer annealing step at 40° C. for 2 min. and a primer extension step at 72° C. for 1 min. This was followed by 28 cycles carried out by a denaturation step at 95° C. for 1 min., followed by a primer annealing step at 56° C. for 1 min. and a primer extension step at 72° C. for 1 min.

The amplified products were run on an agarose gel, isolated and ligated into pT7Blue(R) using a TA cloning kit manufactured by Novagen. The nucleotide sequence of the clones was determined by the Sanger dideoxynucleotide chain reaction termination reaction, using Sequenase™ version 2.0 manufactured by U.S. Biochemical.

In order to obtain the remaining 5' DNA sequence of SEQ ID NO:5 (peptide A cDNA), cDNA was obtained from mRNA as described above. Following the reaction, the excess primers and nucleotide were removed by ultra filtration through a Centricon-100 filter unit manufactured by Amicon. The cDNA was then washed two times with 2 mls of 0.1× TE (1 mM Tris, pH 7.5/0.1 mM EDTA). The washed cDNA obtained was concentrated on a Savant Instruments Speed-Vac and resuspended in a final volume of 15 μl of sterile distilled water. A poly-deoxyguanylate (poly-dG) tail was then added to the 5' end of the cDNA using 12 units of terminal deoxynucleotidyl-transferase from BRL, 4 μl of 5× reaction buffer also from BRL and 1 μl of 10 mM solution of deoxyguanylate triphosphate (dGTP). After a 15 min. incubation at 37° C., the dG- tailed cDNA was ethanol precipitated and resuspended in 20 μl of sterile distilled water. The PCR-RACE reaction was performed under the same reaction conditions used above except that different primers were used. The primer pairs consisted of a poly d(C) tailed oligonucleotide, which contained a Sal I endonuclease recognition signal, and a gene-specific oligonucleotide spanning a Kpn I endonuclease recognition sequence found in the coding sequence of the SEQ ID NO:5 (peptide A cDNA) cDNA. The amplified products were isolated from an agarose gel, digested with Sal I and Kpn I endonucleases and ligated into the plasmid pBluescriptKS™ digested with the same endonucleases. The clones obtained were sequenced under the same reaction conditions described above.

Finally, the two clones which together comprised the entire SEQ ID NO:5 (peptide A cDNA) cDNA were fused at the internal Kpn I endonuclease site to generate a cDNA that contained the entire coding region for peptide SEQ ID NO:5 (peptide A cDNA).

EXAMPLE 8

Recombinant Baculovirus Containing SEQ ID NO:5 (peptide A cDNA)

A plasmid harboring the SEQ ID NO:5 (peptide A cDNA) cDNA, or any protein modification thereof, is digested with endonucleases that release the cDNA from the plasmid. The cDNA can then be run and isolated from an agarose gel using any of several methods well known in the art. If, for example, the baculovirus expression vector employed for the expression of AaIT toxin is used, the cDNA is blunted with either the large fragment of DNA polymerase I or T4 DNA polymerase, depending on the overhang left by the endonuclease used above. Bam HI linkers are then ligated to both ends of the cDNA. The expression vector pAcUW2(B) is then digested with Bgl II endonuclease and dephosporylated with calf intestine alkaline phosphatase or other phosphatase. McCutchen, B. F. et al. *Bio/Technology* 9, 848–852

(1991). The purified Bam HI linked SEQ ID NO:5 (peptide A cDNA) and pAcUW2(B) is then ligated to form the completed SEQ ID NO:5 (peptide A cDNA) expression vector. Detailed instruction for all the techniques used above may be found in Maniatis et al. (1982). *Molecular cloning a laboratory manual*; Cold Spring Harbor Laboratory, Cold Spring Harbor or similar manual.

Next, Sf-9 cells (ATCC#CRL1711) are co-transfected by calcium phosphate precipitation with the SEQ ID NO:5 (peptide A cDNA) expression vector and a polyhedrin-negative *Autographa californica* nuclear polyhedrosis virus (AcNPV) DNA, such as the RP8 transfer vector. Matsuura et al. J. Gen. *Virol* 68:1233–1250 (1987). The supernatant is isolated 5 days post-transfection and subjected to plaque purification. The homologously recombined recombinant baculovirus forms polyhedrin-negative plaques that are isolated and purified according to the method of Summers and Smith. Summers, M. D. and Smith, G. E. *Texas Agricultural Experimental Station Bulletin,* 1555, 1–56 (1987).

The purified recombinant plaques are then tested for biological activity. Proliferating Sf-9 cells are infected with recombinant baculovirus at a multiplicity of infection of between 1:1 and 1:100 determined empirically. The supernatant is collected 7 days post infection. The pelleted cells are resuspended in 1% SDS and vortexed for 5 minutes to remove polyhedra. After three washes, the viral titer is determined. Approximately $1\times10^6$ recombinant plaque forming units are injected into larvae and the toxic effect of the virus encoding SEQ ID NO:5 (peptide A cDNA) is determined relative to wild-type baculovirus similarly treated. Oral infection is assayed by inoculating the larval diet with similar amounts of recombinant and wild-type baculovirus and observing their relative effects.

EXAMPLE 9

Recombinant Baculovirus Containing SEQ ID NO:6 (peptide B cDNA)

A recombinant baculovirus harboring the SEQ ID NO:6 (peptide B cDNA) cDNA, or any protein modification thereof, may be constructed by the method described in Example 8 employed for the SEQ ID NO:5 (peptide A cDNA) cDNA.

EXAMPLE 10

Recombinant Baculovirus Containing SEQ ID NO:7 (peptide C cDNA)

A recombinant baculovirus harboring the SEQ ID NO:7 (peptide C cDNA) cDNA, or any protein modification thereof, may be constructed by the method described in Example 9 employed for the SEQ ID NO:5 (peptide A cDNA).

EXAMPLE 18

Mammalian toxicity of Calisoga toxins

Peptide A was tested for mammalian toxicity by intraperitoneal injection in mice. Two male Balb-C mice (~25 grams each) were injected with peptide A in physiological saline, at a dose of 50 micrograms per mouse (~2 mg/kg). Two control mice were injected with an equal volume of saline carrier. The mice were observed continuously for 1.5 hours, and periodically thereafter. No effects were noted at any time up to 120 hours after treatment, when observations were discontinued. These results indicate that insecticidal Calisoga peptides may have considerable selectivity for insects.

SUMMARY

The present invention relates to three insecticidally effective proteins isolated from the spider, Calisoga, characterized by their neurotoxic effect on insects pests. When small, insecticidally effective, quantities of these proteins are administered to selected insects, the insects are paralysed or killed.

As described above, the present invention also relates to the cloning of these peptides using routine recombinant DNA technology. The cDNA sequences of the peptides has been shown to code for precursor proteins which are 80 amino acids in length. The first 41 amino acids are a putative signal sequence and a propeptide sequence. The mature protein comprises the remaining 39 amino acids.

The present invention also provides methods for modifying and improving the described peptides for use as insecticidal agents. In addition, the present invention relates to the use of these proteins as agents for combating insect pests. Large quantities of these peptides may be obtained using known recombinant technology methods. The peptides can be engineered into an expression vector which is then inserted into either a prokaryotic host, such as *E. coli*, or a eukaryotic host, such as insect cells. The isolated protein may then be applied directly to the plant or animal sought to be protected from insect pests.

As an alternative, as described above, the peptides may be engineered into a natural pathogen of insects such as Bacillus or baculovirus. The recombinant pathogens can be utilized to transfer the peptide directly into the insect pests. These recombinantly engineered pathogens will have significantly increased toxicity.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A fraction of whole Calisoga spider venom comprising a fraction which is neurotoxic to *Heliothis virescens*, said neurotoxic fraction comprising SEQ NO:1, SEQ ID NO:2 or SEQ ID NO:3.

2. A spider venom fraction as defined in claim 1 comprising SEQ ID NO:1.

3. A spider venom fraction as defined in claim 1 comprising SEQ ID NO:2.

4. A spider venom fraction as defined in claim 1 comprising SEQ ID NO:3.

5. A substantially purified insecticidally effective peptide isolated from Calisoga spider venom which is neurotoxic to insect pests, has an observed molecular mass of about 4300 amu and a $PD_{50}$ in *Heliothis virescens* greater than about 2.37 μg/g.

6. A peptide as defined in claim 5 comprising SEQ ID NO:1.

7. A peptide as defined in claim 5 comprising SEQ ID NO:2.

8. A peptide as defined in claim 5 comprising SEQ ID NO:3.

9. An insect toxin comprising the amino acid sequence encoded by SEQ ID NO:5 or fragment thereof which is toxic to insects.

10. An isolated, extrachromosomal nucleic acid which encodes the toxin or toxic fragment of claim 9.

11. A nucleic acid sequence as defined in claim 10 wherein the nucleic acid sequence is subcloned into a plasmid.

12. A nucleic acid sequence as defined in claim 10 wherein the nucleic acid sequence is subcloned into a prokaryotic, eukaryotic or baculovirus expression vector.

13. A nucleic acid sequence as defined in claim 10 wherein the nucleic acid sequence is stably or transiently incorporated into a prokaryotic or eukaryotic host cell.

14. An nucleic acid sequence as defined in claim 10, wherein the nucleic acid sequence is stably or transiently incorporated into an isolated cell of a baculovirus host.

15. An insect toxin comprising the amino acid sequence of SEQ ID NO:6 or a functional derivative or fragment thereof which is toxic to insects.

16. An isolated, extrachromosomal nucleic acid which encodes the toxin or toxic fragment of claim 15.

17. A nucleic acid sequence as defined in claim 16 wherein the nucleic acid sequence is subcloned into a plasmid.

18. A nucleic acid sequence as defined in claim 16 wherein the nucleic acid sequence is subcloned into a prokaryotic, eukaryotic or baculovirus expression vector.

19. A nucleic acid sequence as defined in claim 16 wherein the nucleic acid sequence is stably or transiently incorporated into a prokaryotic or eukaryotic host cell.

20. A nucleic acid sequence as defined in claim 15, wherein the nucleic acid sequence is stably or transiently incorporated into an isolated cell of a baculovirus host.

21. An insect toxin comprising the amino acid sequence encoded by SEQ ID NO:7 or fragment thereof which is toxic to insects.

22. An isolated, extrachromosomal nucleic acid which encodes the toxin or toxic fragment of claim 21.

23. A nucleic acid sequence as defined in claim 22 wherein the nucleic acid sequence is subcloned into a plasmid.

24. A nucleic acid sequence as defined in claim 22 wherein the nucleic acid sequence is subcloned into a prokaryotic, eukaryotic or baculovirus expression vector.

25. A nucleic acid sequence as defined in claim 22 wherein the nucleic acid sequence is stably or transiently incorporated into a prokaryotic or eukaryotic host.

26. A nucleic acid sequence as defined in claim 22, wherein the nucleic acid sequence is stably or transiently incorporated into an isolated cell of a baculovirus host.

27. A substantially purified insecticidally effective peptide isolated from Calisoga spider venom which is neurotoxic to insect pests, has an observed molecular mass of about 4300 amu and a $PD_{50}$ in *Heliothis virescens* of about 3.7 μg/g.

28. A method of controlling insects comprising exposing insects to an insecticidally effective quantity of the peptide of claim 27.

29. A substantially purified insecticidally effective peptide isolated from Calisoga spider venom which is neurotoxic to insect pests, has an observed molecular mass of about 4300 amu and a $PD_{50}$ in *Heliothis virescens* of about 4.5 μg/g.

30. A method of controlling insects comprising exposing insects to an insecticidally effective quantity of the peptide of claim 29.

31. A substantially purified insecticidally effective peptide isolated from Calisoga spider venom which is neurotoxic to insect pests, has an observed molecular mass of about 4300 amu and a $PD_{50}$ in *Heliothis virescens* of about 2.37 μg/g.

32. A method of controlling insects comprising exposing insects to an insecticidally effective quantity of the peptide of claim 31.

33. A method of controlling insects comprising exposing insects to an insecticidally effective quantity of the toxin or toxic fragment of claim 9.

34. A method of controlling insects composing exposing insects to the recombinant baculovirus host cell of claim 14.

35. A method of controlling insects comprising exposing insects to an insecticidally effective quantity of the of the toxin or toxic fragment of claim 15.

36. A method of controlling insects comprising exposing insects to the recombinant baculovirus host cell of claim 20.

37. A method of controlling insects comprising exposing insects to an insecticidally effective quantity of the of the toxin or toxic fragment of claim 21.

38. A method of controlling insects comprising exposing insects to the recombinant baculovirus host cell of claim 26.

* * * * *